United States Patent [19]

Steer et al.

[11] Patent Number: 5,902,295
[45] Date of Patent: May 11, 1999

[54] OSTOMY COUPLING

[75] Inventors: Peter L. Steer, Sussex; Keith G. M. Hollands, Sompting, both of United Kingdom

[73] Assignee: Bristol-Myers Squibb Company, New York, N.Y.

[21] Appl. No.: 08/631,393

[22] Filed: Apr. 12, 1996

[30] Foreign Application Priority Data

Apr. 13, 1995 [GB] United Kingdom .................... 9507666
Aug. 30, 1995 [GB] United Kingdom .................... 9517666

[51] Int. Cl.⁶ ....................................................... A61F 5/445
[52] U.S. Cl. ............................ 604/339; 604/332; 604/338
[58] Field of Search ..................................... 604/283, 332, 604/338, 339, 342

[56] References Cited

U.S. PATENT DOCUMENTS

| | | | |
|---|---|---|---|
| 5,180,377 | 1/1993 | Holtermann | 604/338 |
| 5,322,522 | 6/1994 | Olsen | 604/338 |
| 5,322,523 | 6/1994 | Olsen | 604/338 |

*Primary Examiner*—Robert A. Clarke
*Attorney, Agent, or Firm*—Stuart E. Krieger

[57] ABSTRACT

An ostomy coupling has first and second coupling members. These can be held together by a springy flexible split locking ring. A plurality of tabs, arranged, e.g., symetrically, on the limbs of the locking ring can be withdrawn generally radially outwardly by movement of the locking ring to permit separation of the two coupling members. The movement of the locking ring which causes withdrawal of the tabs may be a vertically upward movement of the ring, or a vertically downward movement. The movement of the locking ring which causes withdrawal of the tabs alternatively may be a deformation of the ring in opposed horizontal directions. Preferably, however, the movement of the locking ring which causes a withdrawal of the tabs is a rotational movement relative to the second coupling member.

20 Claims, 3 Drawing Sheets

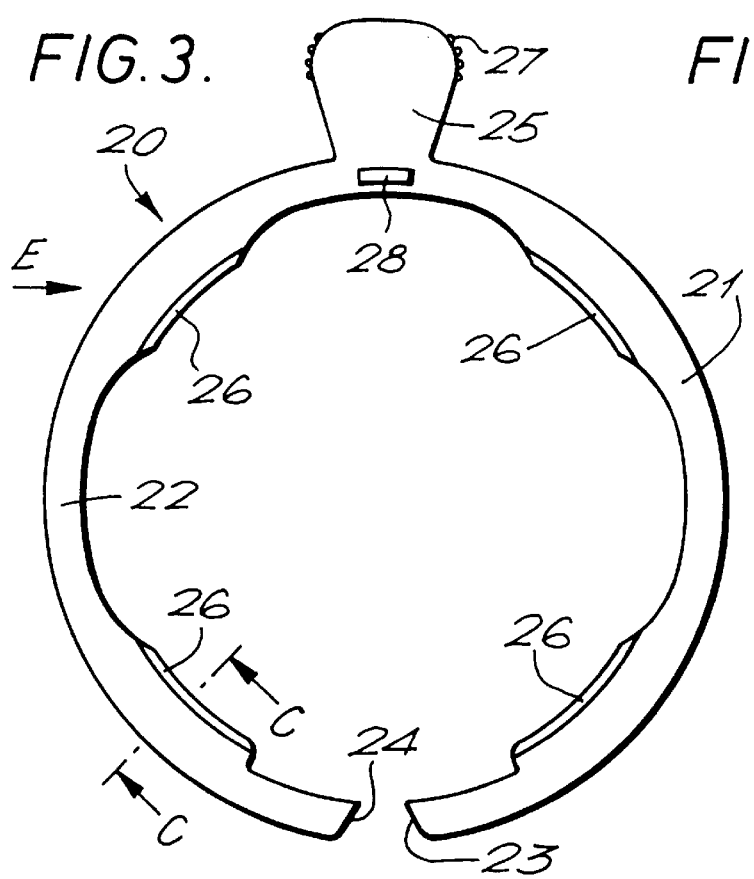
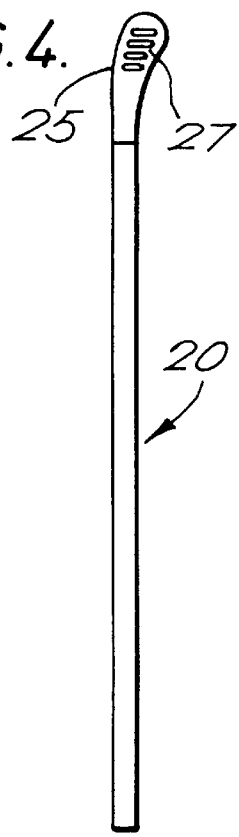
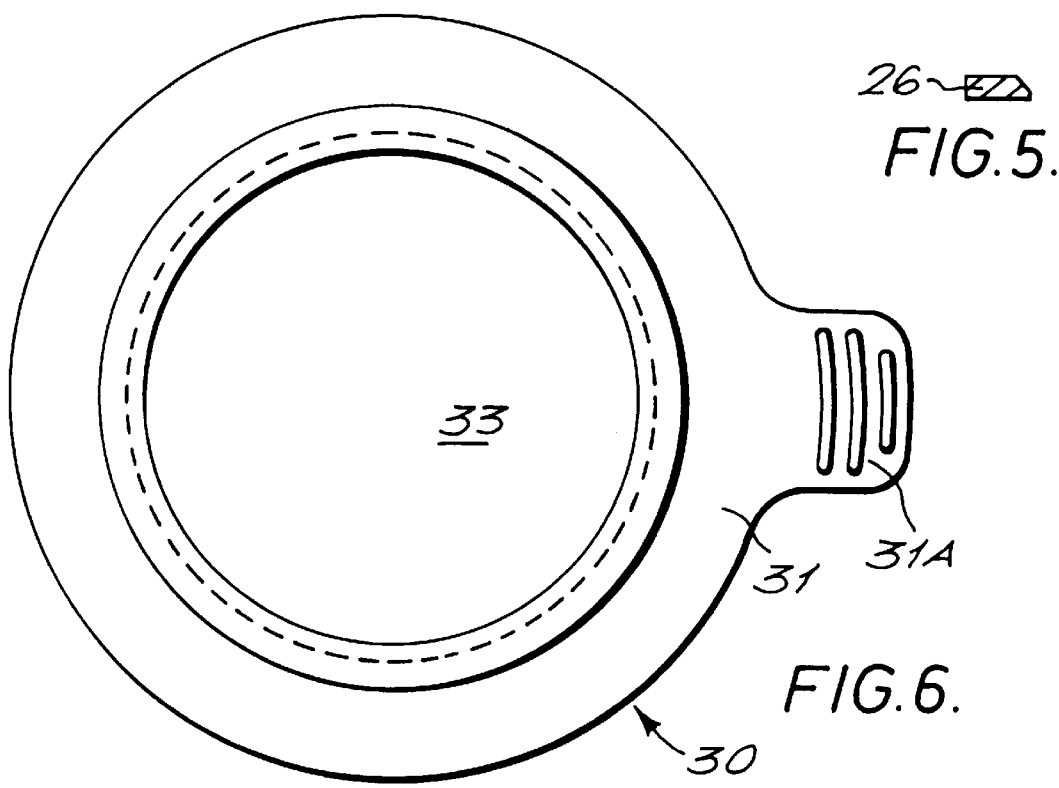

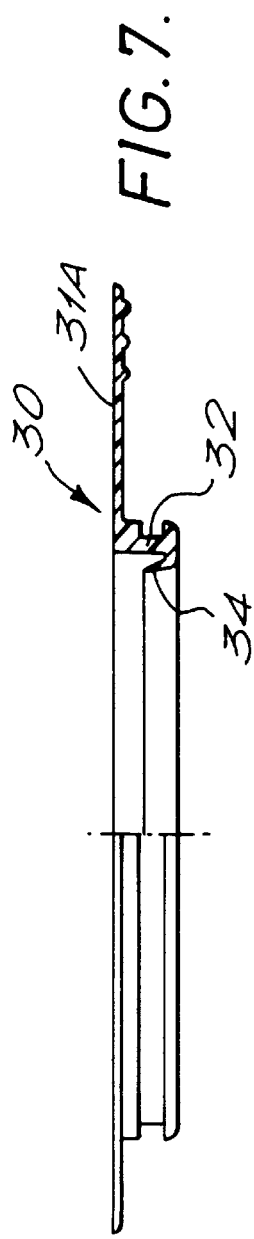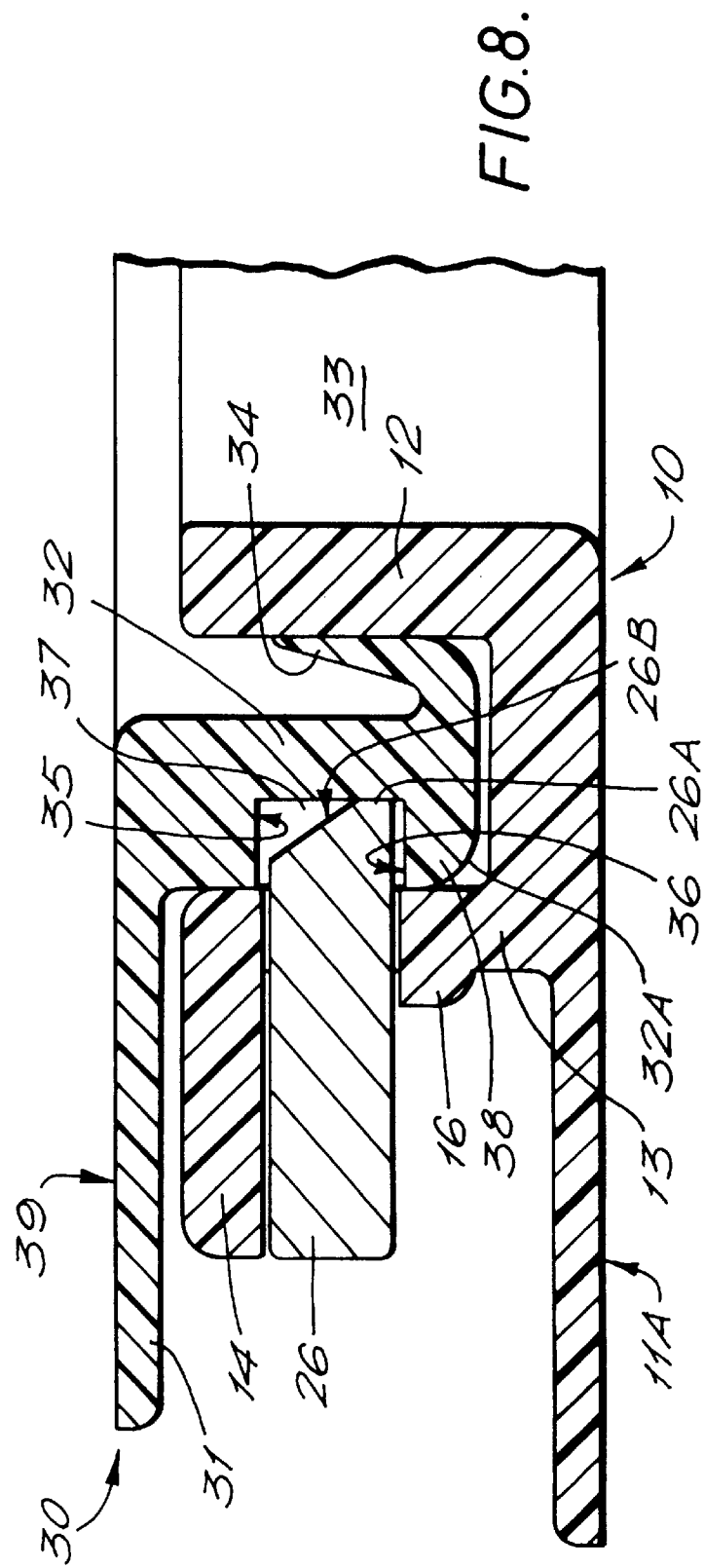

OSTOMY COUPLING

BACKGROUND OF THE INVENTION

This invention relates to an ostomy coupling.

Ostomy couplings are used to connect and disconnect a bag for receiving a stomal discharge to and from a medical grade adhesive pad which is applied to the peristomal area of the skin of the wearer. Many designs of ostomy coupling are known. One which has enjoyed considerable commercial success is described and claimed in U.K. Patent No. 1,571, 657.

An ostomy coupling in which unlocking of two coupling parts is achieved by deforming a ring in the form of a closed loop is disclosed in our U.K. Patent Application No. 9409037.0, filed May 6, 1994.

It has been proposed by Kubo, in Japanese Utility Model No. 62-11610, published February 1985, that an ostomy device should have a double female ring structure which can interengage with a male ring. The male ring may be on the bag and the female ring on a skin-attachable adhesive pad, or vice-versa. The outer ring on the female ring is circular and flexible and has a pair of inwardly-extending catches at opposite ends of a diameter. By pressing on two diametrically extending lugs, whose diameter is substantially at right angles to the diameter joining the catches, the outer female ring is deformed so that the catches are caused to move radially outwardly, so permitting separation of the two coupling parts.

This arrangement, though perhaps operable in theory, has serious disadvantages in practice, for example (i) to connect or disconnect it is necessary to hold the coupling at four places, approximately spaced at 90° intervals around the periphery, (ii) pressing on two diametrically opposed regions will tend to bend the coupling out of its normal plane and the forces applied may easily cause the body side pad to be partially (or wholly) detached from the skin of the wearer, also the need to press in both ends of the diameter fully, and simultaneously, means that releasing the bag-side coupling is subject to uncertainty, (iii) the repeated attachment and withdrawal of the bag-side coupling part will cause the o-ring (provided to prevent escape of excreted matter between the male and female rings) to become worn, so compromising its sealing qualities with potentially highly embarrassing and undesirable results, (iv) the wearer may find it difficult to determine whether or not the two coupling parts are properly engaged, (v) the accuracy and forces needed for manipulation to connect or disconnect will be well beyond the capability of an infirm, confused, elderly or impatient wearer; (vi) it is hard to be sure that the appliance is properly locked; and (vii) in the case of large sizes, the old and infirm will find it physically difficult to span with their hand and push in diametrally opposed regions of the ring.

In U.S. Pat. No. 5,180,377 there is disclosed an ostomy coupling in which a bag-side coupling attached to an ostomy pouch can be held onto to a body-side member by a third member which is substantially circular, deformable, and clamps or grips the bag side coupling when it is tightened. In practice, the diameter of the third member is reduced by operation of a mechanical control mechanism, some of whose parts are attached to the third member. While it may be true, as the patentee states, that a sealed mechanical connection of bag- and body-side couplings can be achieved using such a mechanism, the overall construction is relatively complex, which of course affects manufacturing costs.

PCT published Applications Nos. WO91/01118 and WO91/01119 relate to an ostomy coupling and to a ring for locking such a coupling. The ring has two free ends which are manually pulled together to tighten the ring circumferentially around bag- and body-side coupling parts whose structure is designed in various ways so that they can inter-engage. This results in a variety of relatively complex designs, likely to be costly to manufacture. Manipulation of such a coupling will potentially give rise to difficulties for infirm, elderly, or non-dexterous persons.

It is an aim of this invention to provide improved designs of ostomy couplings which embody a springy or resilient split ring as a locking ring. That is, the ring is generally circular in form but has a single gap therein, subtending a small angle, e.g. 5 to 15°.

SUMMARY OF THE INVENTION

According to the present invention, there is provided an ostomy coupling in which first and second coupling members are held together by a springy flexible split locking ring and in which a plurality of tabs, symmetrically arranged on each limb of the locking ring, can be withdrawn generally radially outwardly by movement of the locking ring to permit separation of the two coupling members.

The movement of the locking ring which causes withdrawal of the tabs is a rotational movement of the ring a short arcuate distance around the axis of rotation of the coupling. The ring preferably has a handle thereon at or near its "top dead centre".

The invention will be better understood from the following non-limiting description of an example thereof given with reference to the accompanying drawings in which:

FIG. 3 is a plan view of a split locking ring forming part of an ostomy coupling according to the invention;

FIG. 4 is a side elevation of the ring looking in the direction "E" of FIG. 3;

FIG. 5 is a cross-sectional view, on the plane C—C of FIG. 3, of the locking ring shown in FIG. 3;

FIG. 6 is a plan view of a second or bag side coupling in accordance with the present invention;

FIG. 7 is a side elevational view partly in section of the second or bag side coupling of FIG. 6.

FIG. 8 is a view in axial cross-section on an enlarged scale, showing the parts of the coupling in assembled condition with the locking ring being shown in its locked position.

DETAILED DESCRIPTION OF THE DRAWINGS

Figure 1:
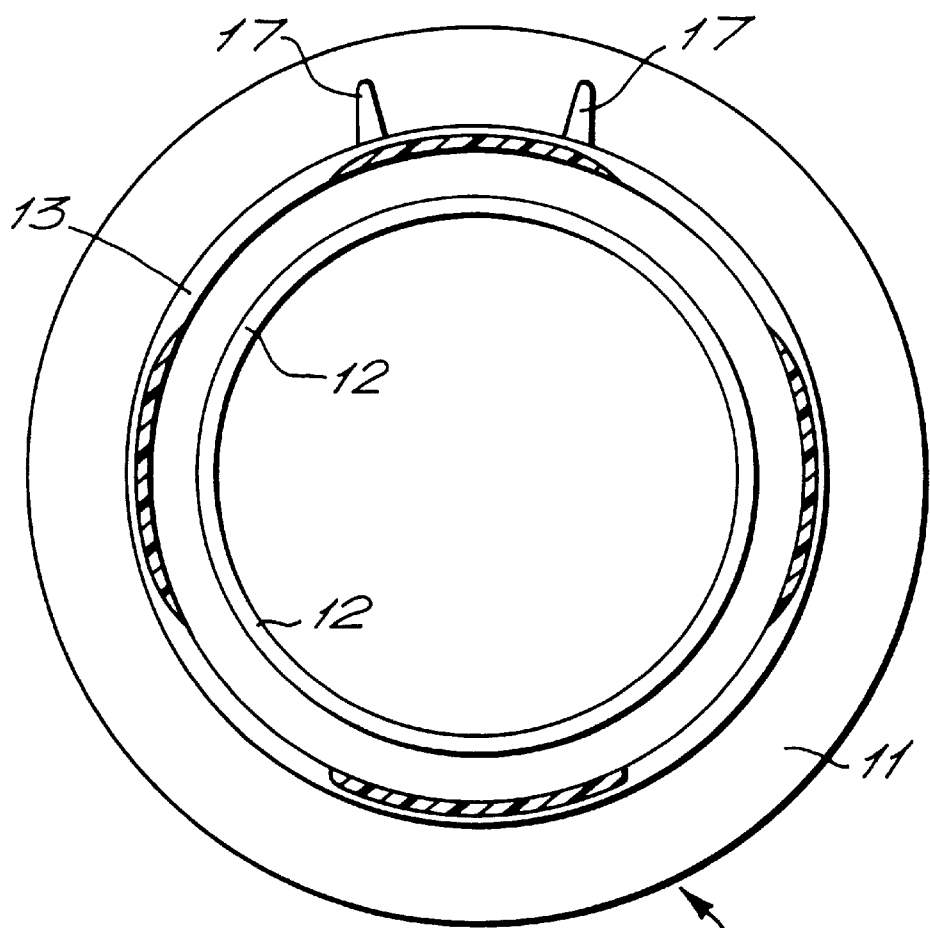
FIG. 1 is a cross-sectional view on the plane B—B of FIG. 2 of an embodiment of the invention, showing a first or body-side coupling member, in plan view.
Figure 2:
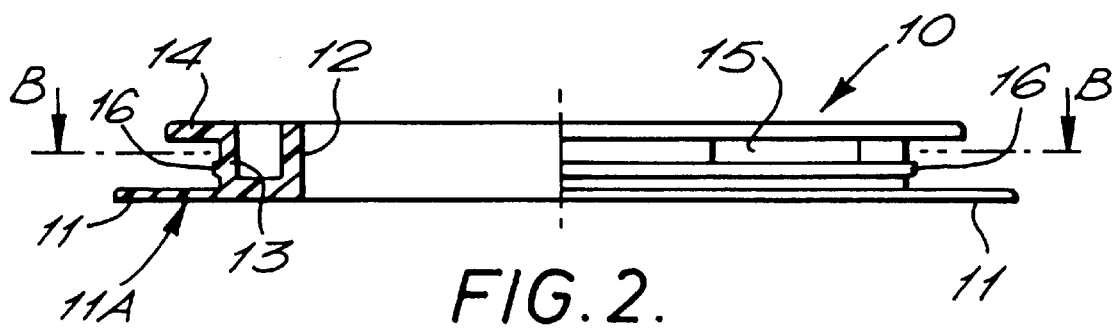
FIG. 2 is an elevation, but with the left-hand half partly in section, of the first coupling member shown in FIG. 1.

In accordance with a preferred embodiment of this invention, there is now described a first coupling member 10 which will normally be a body-side coupling member. This comprises a lower flange 11, having a surface 11A to which may be attached a medical grade adhesive pad. Such medical grade adhesive pads are known, and are used to attach the ostomy appliance to the skin of the wearer in the peristomal region. The pad comprises a base which is preferably a thin film of polymeric material such as polyethylene and an adhesive layer situated on the rear surface of the base. Such an adhesive layer is preferably formed as a homogeneous blend of one or more pressure-sensitive viscous or elastomeric materials having intermittently dispersed therein one or more water-soluble or swellable hydrocolloid gums and may also include one or more thermoplastic elastomers and/or one or more swellable cohesive strengthening agents. The first coupling member 10 also has a radially inner wall 12, and a radially outer wall 13. Together these walls, with flange 11, define an annular channel, there being a radially outwardly extending flange 14, substantially parallel to the flange 11, and attached to or integral with the annular channel. The channel is best seen in the left-hand portion of FIG. 2. The wall 13 has therein a plurality of apertures 15, four in number, which are located to permit passage of respective locking blades 26 through the apertures, as seen in FIG. 8. A radially outstanding rim 16, of shallow radius, is disposed on the outer surface of the wall 13. As seen in FIG. 1, a pair of stops 17 are located (in the position when the ostomy coupling member is being worn) at the upper region of the member and at respective positions such that the angle subtended between them is approximately 30°. Of course other suitable angles may be used instead of 30°, as will be understood by one skilled in the art.

FIGS. 3, 4 and 5 illustrate a preferred form of locking ring 20 for use in an ostomy appliance according to the invention. This ring is a split ring, that is, it comprises a pair of limbs 21 and 22 having free ends 23 and 24, these free ends in the normal rest or unstressed position of the ring being spaced from each other by a distance that subtends an angle of approximately 10°. Integral with each limb 21 of the locking ring, are locking blades 26 which extend generally radially inwardly. At the top of the locking ring 20, a handle 25 having gripping ribs 27 is provided to enable the wearer to rotate the locking ring relative to the coupling member 10. A stud 28 projects from the split ring 10 into the gap between the stops 17 (when the parts are assembled).

The third element of the ostomy appliance is the second coupling ring 30 which normally will be the bag-side coupling member. This comprises a radially extending flange 31 integral with a substantially cylindrical wall 32 which surrounds a stomal orifice 33. An ostomy bag or pouch is attached in any suitable manner to a surface 39 of the ring 30. Extending inwardly from one side of the wall 32 is a flexible resilient sealing strip 34 whose main function is to prevent leakage of liquids or other waste material through the coupling when the bag-side coupling member is attached to the body-side coupling member and locked thereon, due to the positioning of the ring 20. Strip 34 also takes up moulding tolerances. On the radially external surface of the wall 32, a groove 37 is provided, bounded by surfaces 35 and 36, there being a rim 38 which serves a locking function in cooperation with the locking blade 26, preventing the coupling members 10 and 30 from being separated from each other in an axial direction. The rim 16 also assists in guiding the locking blades 26 into and out of the groove 13, when the locking ring 20 is moved in a rotary direction. This rotary movement is limited in either rotary direction by the abutment of a stop 28 on the locking ring 20 with respective stops 17 on the first coupling member 10. A grip tab 31A is made in one piece with the flange 31 of the second coupling member 30. Grip tabs are well known in ostomy couplings and grip tab 31A forms no part of the novelty of the present invention.

In operation, given that the coupling members and the locking ring are assembled together as shown in FIG. 8, and assuming that an ostomate wishes to remove the second coupling member and the pouch attached thereto, he or she would then grasp the handle 25 between finger and thumb and shift it to cause the locking ring to make a rotating movement, this movement shifting the stud 28 from engagement with one of the stops 17 and moving it into engagement with the other of the stops 17. As a consequence the locking ring is rotated relative to the first and second coupling members which remain non-rotative. The blades 26, due to their curved surfaces 26A, are forced radially outwardly of the respective apertures 15. This causes the blade 26 as seen in FIG. 8 to move horizontally in a direction towards the right as seen in the Figure, until the inner edge 26A of that blade is shifted to be clear of the annular channel occupied by the second coupling member 30. The coupling member 30 and the pouch attached thereto may then be axially withdrawn from the first coupling member 10.

The ostomate may then if he wishes return the handle 25 to its original position but if this is not done, the chamfer surface 26B in combination with the curved surface 32A enables a new second coupling ring to be axially pushed into the first coupling ring against the resilience of the locking ring 20.

It will be appreciated that variations may be made without departing from the invention. For example, while reference has been to circular first and second coupling members, coupling members of other closed loop forms, e.g. oval, could be employed subject to certain adjustments to the design. While the first coupling member has been referred to as a body-side coupling member and the second as a bag-side coupling member, these parts could be reversed if desired. That is to say, coupling member 10 could be attached to a pouch and coupling member 30 could be attached to a pad of medical grade adhesive on the skin of the ostomate. While four locking blades 26 have been shown in the above drawings, a different number of locking blades, and a corresponding different number of apertures, could be employed instead. Other suitable detents or movement limiting members could be employed instead of the stop 17 and stud 28, without departing from the invention.

What is claimed is:

1. An ostomy coupling comprising:
   first and second coupling members capable of being releasably coupled together; and
   a resilient split locking ring for releasably locking said first and second coupling members, said locking ring having two limbs which together extend substantially around said ring, said locking ring being expandable at said split to an expanded position upon rotation of said ring to permit coupling and uncoupling of said first and second coupling members and resiliently contractible from said expanded position to a resting position for locking said first and second coupling members together.

2. The ostomy coupling of claim 1 wherein said locking ring includes a plurality of tabs extendable through said first coupling member to grip said second coupling member so as to lock said coupling members together.

3. The ostomy coupling of claim 1 wherein said first coupling member has at least one aperture and said locking ring has at least one locking blade extendable through said aperture for gripping said second coupling member and locking said coupling members together.

4. The ostomy coupling of claim 3 wherein said second coupling member has at least one groove for receiving said locking blade and locking said coupling members together.

5. The ostomy coupling of claim 1 wherein said locking ring includes a plurality of locking blades extending radially inwardly.

6. The ostomy coupling of claim 5 wherein said first coupling member has an aperture for accommodating each locking blade and for permitting each locking blade to be extended through and retracted from said aperture.

7. The ostomy coupling of claim 5 wherein said locking blades have a curved surface to facilitate retraction from said aperture upon expansion of said locking ring.

8. The ostomy coupling of claim 1 wherein said locking ring includes a handle manipulatable to rotate said locking ring.

9. The ostomy coupling of claim 1 wherein said locking ring includes two limb portions each having a free end and a handle on said locking ring between said free ends, said handle being manipulatable to rotate said locking ring.

10. The ostomy coupling of claim 9 wherein said free ends are spaced from each other by a distance that subtends an angle of about 10°.

11. The ostomy coupling of claim 1 wherein said first coupling is a body side coupling member having an annular channel defined by two sidewalls and a floor, said channel surrounding a stomal orifice, and said second coupling member is a bag side coupling member having a flexible resilient sealing strip which bears against a sidewall of said annular channel minimizing leakage of bag contents when said coupling members are coupled together.

12. The ostomy coupling of claim 1 wherein said locking ring has a plurality of tabs, said first coupling member has an aperture for each tab, said tabs being extendable through said apertures to grip said second coupling member and lock said coupling members together, and withdrawable from said apertures to permit separation of said coupling members.

13. The ostomy coupling of claim 12 wherein said tabs are symmetrically arranged on said locking ring.

14. The ostomy coupling of claim 13 wherein said locking ring is rotatable a predetermined distance around said first coupling member.

15. The ostomy coupling of claim 14 wherein a first and second stop on said first coupling member limits rotation of said locking ring.

16. The ostomy coupling of claim 15 wherein said handle includes a stud contactable with at least one said stops for limiting rotation of said locking ring.

17. The ostomy coupling of claim 14 wherein the gap between said stops subtends an angle of about 30°.

18. The ostomy coupling of claim 12 wherein said aperture has a rim, said rim assisting in guiding a portion of said locking ring into and out of said groove of said second coupling member for locking and unlocking, respectively, said first and second coupling members.

19. The ostomy coupling of claim 18 wherein said second coupling member has a projection engaging said annular channel of said first coupling member, said projection including said sealing strip, said projection having surfaces which facilitate the axial pushing of said first and second coupling members together against said resilience of said locking ring.

20. The ostomy coupling of claim 1 wherein said second coupling has a groove, said groove engageable by a portion of said locking ring for locking said first and second coupling members together.

* * * * *